United States Patent [19]

Karbowski et al.

[11] Patent Number: 4,800,082

[45] Date of Patent: Jan. 24, 1989

[54] SUSTAINED RELEASE MICROBIOLOGICAL CONTROL COMPOSITION

[75] Inventors: Robert J. Karbowski, Sanford; Anita S. Erickson; Charles D. Gartner, both of Midland, all of Mich.; Kathleen A. Roy, Dunwoody, Ga.

[73] Assignee: The Dow Chemical Company, Midland, Mich.

[21] Appl. No.: 29,017

[22] Filed: Mar. 23, 1987

[51] Int. Cl.[4] .................... A01N 25/08; D21D 3/00; C02F 1/76
[52] U.S. Cl. .................... 424/409; 424/464; 424/468; 162/161; 210/754
[58] Field of Search ............ 424/409, 419, 464, 468, 424/489; 206/528; 210/754; 162/161

[56] References Cited

U.S. PATENT DOCUMENTS

| | | | |
|---|---|---|---|
| 4,007,258 | 2/1977 | Cohen et al. | 424/409 |
| 4,022,605 | 5/1977 | Konya et al. | 71/67 |
| 4,241,080 | 12/1980 | Burk | 424/304 |
| 4,284,444 | 8/1981 | Bernstein | 156/60 |

FOREIGN PATENT DOCUMENTS 2111388  7/1983  United Kingdom ................ 424/409

Primary Examiner—Thurman K. Page
Attorney, Agent, or Firm—Craig E. Mixan; Ronald G. Brookens

[57] ABSTRACT

A solid antimicrobial composition of a halogenated amide such as 2,2-dibromo-3-nitrilopropionamide and a suitable hydrophilic polymer such as hydroxypropyl methyl cellulose with the optional presence of a compression agent and a mold release agent. The invention is also directed to a method for biological control in an aqueous industrial system by contacting the system with the antimicrobial composition.

28 Claims, No Drawings

SUSTAINED RELEASE MICROBIOLOGICAL CONTROL COMPOSITION

BACKGROUND OF THE INVENTION

This invention relates to solid, non-medicinal, sustained release, antimicrobial compositions which comprise a halogenated amide as the active (i.e., antimicrobial) ingredient and a suitable hydrophilic polymer.

Halogenated amides such as 2,2-dibromo-3-nitrilopropionamide are well-known antimicrobials useful in a variety of antimicrobial applications. See, for example, U.S. Pat. Nos. 2,419,888; 3,439,658; 4,241,080; 3,350,164; 3,403,174; 3,647,610; 3,649,166; 3,928,575; Belgian Pat. No. 668,336; and Wolf et al., "2,2-Dibromo-3-Nitrilopropionamide, A Compound with Slimicidal Activity," Applied Microbiology, Vol. 24, No. 4, pp. 581–584 (1972).

Halogenated amides are known to rapidly degrade under use conditions. See, for example, U.S. Pat. No. 3,689,660 and "Rates and Products of Decomposition of 2,2-Dibromo-3-Nitrilopropionamide," Exner et al., J. Agr. Food Chem., Vol. 21, No. 5, pp. 838–842 (1973). This rapid degradation is a beneficial environmental feature; however, the rapid degradation is a severe detriment when biocidal persistence is desired or necessary.

Although it has long been desired in the antimicrobial field to have a composition and/or method to increase the persistence of halogenated amide antimicrobials, heretofore such compositions and/or methods have not been available. The present invention provides for a means of meeting the long felt need in the art by use of compositions containing halogenated amide antimicrobials and hydrophilic polymers.

Polymers suitable for use in the present invention, such as natural and synthetic hydrophilic cellulosic polymers, are known polymers. See, for example, U.S. Pat. Nos. 4,429,120; 4,369,172; and 3,839,319. However, use of such polymers with halogenated amide antimicrobials to obtain solid compositions of increased biocidal persistence has been heretofore unknown. The method of the present invention provides for an unexpected increase in antimicrobial efficiency relative to current state of the art methods of use.

SUMMARY OF THE INVENTION

The present invention is directed to a solid, non-medicinal, antimicrobial composition providing for sustained release of the active ingredient (i.e., the halogenated amide) when used in industrial aqueous systems. More specifically, the present invention is directed to a solid composition comprising:
(a) about 1 to about 90 percent by weight of a halogenated amide antimicrobial compound,
(b) about 10 to about 80 percent by weight of a suitable hydrophilic polymer,
(c) about 0 to about 80 percent by weight of a compression agent, and
(d) about 0 to about 10 percent by weight of a mold release agent.

The present invention is also directed to a method for biological control in an aqueous industrial system in need of such control comprising contacting said system with an antimicrobially effective amount of the solid antimicrobial composition.

The terms "antimicrobial compound" and "halogenated amide antimicrobial" are used interchangeably herein and refer to halogenated amides which function as biocides (i.e., compounds which inhibit the growth of, or kill, microorganisms such as bacteria, molds, yeasts, algae, protozoa, etc.).

The term "effective amount" refers to that amount of the solid antimicrobial composition of the present invention that provides for biological control in an aqueous industrial system. The term "biological control" or "biologically controlling" refers to prevention, reduction, or elimination of any adverse consequences such as slime formation, corrosion, odor production, etc., in aqueous industrial systems that are directly, indirectly, or otherwise due to the presence and/or growth of microorganisms.

Those aqueous industrial systems contemplated for application of the method of the present invention are those aqueous industrial systems susceptible to the growth or presence of microorganisms; for example, cooling towers, pulp and paper mills, metalworking fluids, air washers, and the like.

The solid antimicrobial compositions of the present inventions and the method of using thereof provide for, inter alia, the following advantages:
1. Simulated persistence of the rapidly degrading halogenated amide compound while in a closed system,
2. Continuous applications to an aqueous industrial system by non-mechanical means without the use of pumps (i.e., an eductor or a similar dispersing apparatus),
3. Relatively constant concentrations of the antimicrobial compound in spite of water turnover in the system,
4. Ease of treatment relative to manual introduction of liquids, and
5. An unexpected improvement in biocidal efficiency relative to the currently practiced application methods.

DETAILED DESCRIPTION OF THE INVENTION

Halogenated amide antimicrobials employed in the practice of this invention are alpha-haloamides such as those disclosed in U.S. Pat. No. 4,241,080; that is, compounds which contain an amide functionality (i.e., a moiety of the formula —C(O)—N<) and which have at least one halogen atom on a carbon atom located adjacent to (i.e., in the alpha position relative to) the carbonyl group (i.e., the —C(O)— group) of such amide functionality. Advantageously, such halogenated amide antimicrobials are halogenated nitrilopropionamides or halogenated malonic diamides having the formula:

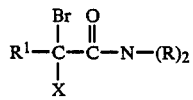

wherein
X is hydrogen, halogen or a cyano radical, i.e., —C≡N, (preferably hydrogen, chlorine or bromine);
each R group is independently hydrogen, a monovalent "saturated hydrocarbon radical" or an inertly substituted monovalent "saturated hydrocarbon radical" or the two R groups are, jointly, a divalent "saturated hydrocarbon radical", or an inertly substituted divalent "saturated hydrocarbon radical", which, taken with the adjacent nitrogen atom, forms a heterocyclic ring having from 4 to about 10 ring members; and $R^1$ is a cyano radical (i.e., $-C\equiv N$) or an amido radical having the formula:

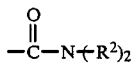

wherein $R^2$ has the same meaning as R. (Preferably $R^1$ is a cyano radical).

As used herein, the term "saturated hydrocarbon radical" refers to a hydrocarbon radical which is free of aliphatic carbon to carbon unsaturation. Thus, such term includes radicals such as alkyl, cycloalkyl, aryl, alkylaryl, arylalkyl, cycloalkylaryl, etc., and excludes radicals such as alkenyl, cycloalkenyl, alkynyl and the like.

As used herein, the term "inertly substituted saturated hydrocarbon radical" refers to a "saturated hydrocarbon radical" having one or more chain linkage or substituent which is "inert" in the sense that such chain linkage or substituent does not readily react with the ingredients of the antimicrobial composition. Suitable inertly substituted saturated hydrocarbon radicals thus include, for example, haloalkyl, haloaryl, halocycloalkyl, aminoalkyl, aminoaryl, aminocycloalkyl, hydroxyalkyl, hydroxyaryl, hydroxycycloalkyl, cyanoalkyl, cyanoaryl, cyanocycloalkyl, and the like.

The aforementioned halogenated amide antimicrobials of the formula I thus include brominated nitrilopropionamides (i.e., compounds of the formula I wherein $R^1$ is a cyano radical), such as 2-bromo-3-nitrilopropionamide, 2-bromo-2,3-dinitrilopropionamide, 2,2-dibromo-3-nitrilopropionamide, N-(n-butyl)-2-bromo-3-nitrilopropionamide; N,N-dimethyl-2,2-dibromo-3-nitrilopropionamide, 2-chloro-2-bromo-3-nitrilopropionamide, N-(n-propyl)-2-iodo-2-bromo-3-nitrilopropionamide, N-methyl-N-ethyl-2-fluoro-2-bromo-3-nitrilopropionamide, N-phenyl-2-cyano-2-bromo-3-nitrilopropionamide, N-cyclohexyl-2,2-dibromo-3-nitrilopropionamide, N-benzyl-2-bromo-3-nitrilopropionamide, N-(2,2-dibromo-3-nitrilopropionoyl)piperidine, and the like.

The aforementioned halogenated amide antimicrobials of the formula I also include mono- and di-bromomalonic diamides (i.e., compounds of the formula I wherein $R^1$ is an amido radical as hereinbefore described), such as 2-bromomalonic diamide, 2,2-dibromomalonic diamide, N-methyl-N'-ethyl-2-chloro-2-bromomalonic diamide, N-phenyl-2-iodo-2-bromomalonic diamide, and the like.

Among the aforementioned halogenated amide antimicrobials, those wherein, in the formula I, $R^1$ is a cyano radical, X is hydrogen, chlorine or bromine and each R is independently hydrogen, lower alkyl (i.e., an alkyl group of from 1 to about 6 carbon atoms) or phenyl are preferred, especially those of the formula I wherein each R independently is hydrogen or methyl and X is hydrogen or bromine. Such halogenated amide antimicrobials include 2-bromo-3-nitrilopropionamide, 2,2-dibromo-3-nitrilopropionamide, N-methyl-2-bromo-3-nitrilopropionamide, N-phenyl-2-bromo-2-chloro-3-nitrilopropionamide, N-methyl-2,2-dibromo-3-nitrilopropionamide, N,N-dimethyl-2-bromo-3-nitrilopropionamide, N,N-diethyl-2,2-dibromo-3-nitrilopropionamide, and N,N-dimethyl-2,2-dibromo-3-nitrilopropionamide.

Also of particular interest are the dibrominated nitrilopropionamides (i.e., the halogenated amide antimicrobials of the formula I wherein X is bromine and $R_1$ is cyano) wherein each R independently is hydrogen, lower alkyl (i.e., containing from 1 to about 6 carbon atoms) or phenyl. Such compounds include 2,2-dibromo-3-nitrilopropionamide, N-(n-butyl)-2,2-dibromo-3-nitrilopropionamide, N,N-dimethyl-2,2-dibromo-3-nitrilopropionamide, N-phenyl-N-methyl-2,2-dibromo-3-nitrilopropionamide and the like; especially 2,2-dibromo-3-nitrilopropionamide.

The suitable hydrophilic polymers useful in the solid composition of the present invention include natural and synthetic water soluble cellulosic polymers such as methyl cellulose and hydroxypropyl methyl cellulose.

Also suitable are natural hydrophilic polymers such as gelatin, maltodextrin, xanthan gum, carrageenan and the like; and synthetic hydrophilic polymers such as carboxymethyl guar, hydroxypropyl guar, carboxymethyl galactomannose, polyvinylpyrrolidone, and the like. It is contemplated that mixtures of suitable hydrophilic polymers are within the scope of the present invention.

Suitable hydrophilic cellulosic polymers are available from the Dow Chemical Company and are known by the trademark Methocel. The following commercially available methylcellulose polymers are suitable for use in the solid composition of the present inventions: Methocel A15LV, Methocel A4C, Methocel A15C and Methocel A4M. The following commercially available hydroxypropylmethylcellulose polymers are suitable for use in the present invention: Methocel K 35LV, Methocel K 100LV, Methocel K 4M, Methocel K 15M, Methocel E 5, Methocel E 15LV, Methocel E50, Methocel E4M, Methocel F50, and Methocel F4M.

The solid compositions of the present invention may also optionally contain a mold release agent. The particular mold release agent used is not critical and can be any suitable mold release agent known in the art that is compatible with the other ingredients. Examples of suitable mold release agents include acid lubricants such as adipic acid, fumaric acid, and stearic acid; polymeric lubricants such as polyfluorocarbon lubricants and polyethylene glycol lubricants; and oils such as encapsulated lubricant oils and encapsulated oil-siloxane polymer mixtures.

The solid compositions of the present invention may optionally contain a compression agent. The particular compression agent used is not critical and can be any suitable compression agent known in the art that is compatible with the other ingredients. Examples of suitable compression agents include dicalcium phosphate dihydrate, lactose, sodium phosphate, calcium sulfate dihydrate, and the like. Lactose is commercially available in several grades and/or forms which are suitable for use in the present invention; however, for larger tablets, spray-dried lactose is preferred such as Fast-Flo Lactose No. 325, (available from Foremost-McKesson).

The amount of antimicrobial compound in the solid compositions of the present invention is between about 1 and 90 percent by weight of the ultimate formulation; a preferred amount is between about 10 and 50 percent; and a most preferred amount is between about 30 and 50 percent. The amount of hydrophilic polymer in the solid composition of the present invention is between about 10 and 60 percent by weight of the ultimate formulation; a preferred amount is between about 20 and 50 percent; and a most preferred amount is between about 20 and 40 percent. The amount of compression agent in the solid compositions of the present invention is between about 0 and 80 percent by weight of the ultimate formulation; a preferred amount is between about 5 and 80 percent; and a most preferred amount is between about 20 and 40 percent. The amount of mold release agent in the solid compositions of the present invention is between about 0 and 10 percent by weight of the ultimate formulation; a preferred amount is between about 0 and 5 percent; and a most preferred amount is between about 0 and 4 percent.

The preferred antimicrobial compound of the solid composition is 2,2-dibromo-3-nitrilopropionamide. The preferred hydrophilic polymer is hydroxypropyl methylcellulose. Preferred compression agents are lactose and dicalcium phosphate dihydrate. A preferred mold release agent is stearic acid.

The solid compositions of the present invention are typically formulated using standard tableting procedures known in the art, e.g., by either wet or dry granulation; therefore, a compression agent and a mold release agent are particularly valuable in such tablet formation procedures. Suitable tablet formation procedures for forming the solid composition of the present invention can be found in, for example, Johnson, "Tablet Manufacture," Chemical Technology Review No. 30, incorporated herein by reference. The tablets typically have an ultimate compression density ranging from about 0.75 g/cubic centimeter (cm)$^3$ to about 1.7 g/cm$^3$.

The solid composition of the present invention in tablet form can be in a variety of shapes, e.g., cylindrical, oval, or spherical. The size of the tablets will vary over a wide range depending upon the particular application and the particular quantities of ingredients and the only limitation placed on the size of the tablets are the limitations of the production equipment employed. However, it is contemplated that for most applications, tablets will vary in size between about 0.1 gram (g) to 10 kilograms (kg); a preferred size is between about 1 g and 1 kg. It is preferred that the solid compositions of the present invention are in the form of non-friable, non-dusting, solid tablets.

The compositions of the present invention exhibit sustained release of the antimicrobial compound which leads to an unexpected level of microbiological control of an aqueous industrial system over time. While it is not desired to be bound by any particular theory or mode of action it is believed that when the solid composition of the present invention is contacted with water, that the hydrophilic cellulosic polymer then forms a gel layer on the outside of the composition (e.g. periphery of a tablet). The gel layer then acts as a barrier which prevents further penetration of water into the composition until such time that the gel layer is eroded and replaced with more gel layer (in essence a moving barrier).

In carrying out the method of the present invention it is contemplated that the solid composition can be placed in a perforated container constructed of a material compatible with said composition, particularly with the antimicrobial compound, such as polyethylene. The container can then be contacted with the industrial water to be treated. This embodiment isolates the active antimicrobial compound from direct contact with metal surfaces which could potentially be corroded by the active antimicrobial compound, and also limits the flow of water over the surface of the composition which allows for an even longer treating time period (i.e., prolonged sustained release).

The tablets in accordance with the present invention can also optionally have an additional thin coating.

The composition of the present invention can optionally contain other inert or active ingredients such as corrosion inhibitors or scale inhibitors.

The present invention is illustrated by the following examples; however, the examples should not be interpreted as a limitation upon the scope of the present invention. All percentages are by weight unless otherwise indicated.

EXAMPLE I

Compositions containing the following ingredients have been prepared as one gram tablets using the procedures described herein and/or procedures known in the art:

1.
 20.0% Methocel K15MP
 37.8% 2,2-Dibromo-3-nitrilopropionamide (DBNPA)
 41.4% Lactose
 0.8% Magnesium stearate 2.
 30.0% Methocel K15MP
 37.8% DBNPA
 31.4% Lactose
 0.8% Magnesium stearate 3.
 20.0% Methocel K100MP
 37.8% DBNPA
 41.4% Lactose
 0.8% Magnesium stearate 4.
 30.0% Methocel K100MP
 37.8% DBNPA
 31.4% Lactose
 0.8% Magnesium stearate 5.
 20.0% Methocel K100MP
 47.8% DBNPA
 31.4% Lactose
 0.8% Magnesium stearate 6.
 30.0% Methocel K100MP
 47.8% DBNPA
 21.4% Lactose
 0.8% Magnesium stearate 7.
 40.0% DBNPA
 30.0% Methocel K15M
 27.0% Dicalcium phosphate dihydrate
 3.0% Stearic acid 8.
 20.0% Methocel A4MP
 37.8% DBNPA
 41.4% Lactose
 0.8% Magnesium stearate 9.
 40.0% DBNPA
 3.0% Stearic acid
 10.5% Methocel K15M
 47.0% Fast-Flo Lactose No. 325

10.
 40.0% DBNPA
 3.0% Stearic acid
 20.0% Methocel K15M 37.0% Fast-Flo Lactose No. 325
11.
 40.0% DBNPA
 3.0% Stearic acid
 30.0% Methocel K15M
 27.0% Fast-Flo Lactose No. 325
12.
 40.0% DBNPA
 3.0% Stearic acid
 40.0% Methocel K15M
 17.0% Fast-Flo Lactose No. 325
13.
 40.0% DBNPA
 3.0% Stearic acid
 50.0% Methocel K15M
 7.0% Fast-Flo Lactose No. 325

EXAMPLE II

Using procedures described herein and/or known in the art, the following compositions are prepared:
1.
 5.0% of DBNPA
 25.0% Methocel K15M
 67.0% Fast-Flo Lactose No. 325
 3.0% Stearic acid
2.
 10.0% DBNPA
 25.0% Methocel K15M
 62.0% Fast-Flo Lactose No. 325
 3.0% Stearic acid
3.
 15.0% DBNPA
 30.0% Methocel K15M
 47.0% Fast-Flo Lactose No. 325
 8.0% Stearic acid

EXAMPLE III

Using procedures described herein and/or known in the art, a series of tablets were perpared containing a constant 40.0 percent DBNPA, a constant 20.0 percent Methocel K15M, a constant 3.0 percent stearic acid, Fast-Flo Lactose No. 325 varying in concentration from 36.0 percent to 36.9 percent, and sodium lauryl sulfate varying in concentration from 0.1 percent to 1.0 percent.

EXAMPLE IV

Using procedures described herein and/or known in the art, compositions were prepared using sodium chloride as a filler to substitute for the antimicrobial compound. Sodium chloride concentration ranged from 39.5 percent to 40.5 percent. Methocel K15M was present in each composition in a range from 29.5 percent to 30.3 percent. The remainder of each composition is as follows:
1.
 27.0% Dicalcium phosphate dihydrate
 3.0% Stearic acid
2.
 27.0% Avicel PH101
 3.0% Stearic acid
3.
 27.0% Fast-Flo Lactose No. 325
 3.0% Stearic acid
4.
 27.0% Sodium phosphate, dibasic
 3.0% Stearic acid
5.
 25.1% Sodium phosphate, dibasic
 3.1% Stearic acid
 1.1% Sodium Lauryl Sulfate
6.
 24.5% Sodium phosphate, dibasic
 3.0% Stearic acid
 3.0% Sodium lauryl sulfate

EXAMPLE V

Using procedures described herein and/or known in the art, compositions were prepared without a compression agent. These compositions are described below.
1.
 20.0% DBNPA
 3.0% Stearic acid
 77.0% Methocel K15M
2.
 30.0% DBNPA
 3.0% Stearic acid
 67.0% Methocel K15M
3.
 40.0% DBNPA
 3.0% Stearic acid
 57.0% Methocel K15M
4.
 50.0% DBNPA
 3.0% Stearic acid
 47.0% Methocel K15M
5.
 60.0% DBNPA
 3.0% Stearic acid
 37.0% Methocel K15M
6.
 70.0% DBNPA
 3.0% Stearic acid
 27.0% Methocel K15M
7.
 80.0% DBNPA
 3.0% Stearic acid
 17.0% Methocel K15M
8.
 90.0% DBNPA
 3.0% Stearic acid
 7.0% Methocel K15M

EXAMPLE VI

Using procedures described herein and/or known in the art, compositions were prepared containing a constant 40 percent DBNPA, a constant 30 percent Fast-Flo Lactose 325, a constant 3 percent stearic acid, and a constant 27 percent polymer in which the polymer was gelatin, maltodextrin, xanthan gum, caroboxymethyl galactomannose, carboxymethyl guar, hydroxypropyl guar, carrageenan, or polyvinylpyrrolidone.

EXAMPLE VII

The method of the present invention was demonstrated in trials in an actual cooling tower system. The method of the present invention was compared to a prior art slug dose method. The cooling tower trials and the results obtained are described below.

Materials and Methods

The cooling system used consisted of a Marley tower (The Marley Cooling Tower Company, Mission, KS) connected through appropriate plumbing to a heat exchanger. The cooling system was located in Midland, MI. The capacity of the system is 1500 gallons. Temperature drop across the tower averages 10 degrees F. The rate of flow in the system is 750 gallons per minute with a variable percent of the total flow going over the tower. Typically, the tower operates at 8 cycles of concentration. The blowdown is controlled by an on-line conductivity meter and make-up water is regulated by a float in the tower basin. Conductivity during the studies varied from a low of approximately 400 microhms to a high of approximately 1250 microhms. Make-up water varied in the range from 2500–4500 gallons per day. Hardness was measured at least weekly and was typically near 800 ppm.

From May 6, 1986, to June 3, 1986, the biocide treatment in the tower consisted of slug doses of DBNPA. Doses of 3 ppm active ingredient were given 7 days per week by metering a 5 percent solution of DBNPA over a 15 minute period. During this time, weather conditions were also recorded. Average daily high and low temperatures were 61.2 and 43.2 degrees F., respectively. Total precipitation during the period was 2.88 inches with a daily range of 0–1.59 inches. On five days per week, samples of water from the system were collected in sterile bottles at a sampling port between the tower and the heat exchanger.

Generally, two samples per day were taken, one immediately prior to DBNPA addition and a second approximately four hours after dosing. Three serial dilutions of the samples were made by adding one milliliter (ml) sample to nine ml of sterile saline. Triplicate 10 microliter inoculations of the samples and dilutions were then made on Trypticase Soy Agar (Difco Laboratories) plates. The plates were incubated for a total of 72 hours at 32 degrees C. At 24 hour intervals, the number of colonies per inoculation were counted (if possible). Organisms per ml of original sample were determined based on the average of the triplicate inoculations. Plate counts read at 24 hours were considered indicative of the fast growing population while 48 and 72 hour counts were considered indicative of the combined fast and slow growers. No attempt was made to classify the organisms.

The tower was treated using timed-release tablets containing DBNPA on two occasions. Tablets weighing approximately 250 grams were prepared and contained 40 percent solid DBNPA, 30 percent Methocel K15M (Dow Chemical), 27 percent dicalcium phosphate dihydrate, and 3 percent stearic acid. Tablets were formed under pressure at 20,000 psi and measured about 2 inches in diameter by 3.25 inches in height. The first time the tower was treated, three tablets were placed in a submerged shallow polyethylene tray situated below the tower fill. This was done to provide moderate water movement by the tablets. The total amount of DBNPA in the three tablets was equivalent to 53 parts per million (ppm) based on total volume of the system. This treatment began an Aug. 11, 1986. Following introduction of the tablets, samples were taken five days per week and treated as before. Visual observations of the tablets were also made at the time of each sampling. During the experiment the average daily high and low temperature readings were 78.7 and 57.2 degrees F., respectively. Total precipitation was 0.32 inches, with a daily range from 0–0.29 inches. During the weekend of Aug. 23–24, 1986, the fan motor malfunctioned, causing the water in the basin to heat to an estimated 150 degrees F. This caused the tablets to melt prematurely.

Because the system had been disrupted during the first treatment, a second set of three tablets was introduced on Sept. 2, 1986. Samples and plate counts were performed as before for a total of four weeks. After this time, the sample tray was removed and the residue and remainder of the tablets were analyzed to determine the quantity of DBNPA which remained. During this portion of the experiment the average daily high and low temperatures were 67.3 and 52.4 degrees F., respectively. Overall precipitation was 19.21 inches, with a daily range of 0–10.11 inches. At the conclusion of this final study the residue and remainder of the tablets were analyzed to determine whether DBNPA remained. This was done by High Performance Liquid Chromatography (HPLC) following shaking the residue with 500 ml acetonitrile.

Results

Microbiological data compiled during the period from May 6, 1986, to June 3, 1986, are shown in Table 1 as Treatment data. Also included in Table 1 are results from samples taken on three days prior to dosing with DBNPA. Where two samples are shown on the same day, the first sample was taken prior to the daily dose and the second taken approximately four hours after dosing. Generally the samples after dosing show a reduction in the number of colony forming units (CFU's). There is also a trend for the population to rebound, i.e., to be much higher by the following day. This is presumably due to the total degradation of DBNPA in a relatively short period of time (as well as loss in the blowdown). The half-life of DBNPA in this tower was determined to be very short, estimated at less than one hour. The plate count data was highly variable. The total dose of DBNPA given to the system during this time was 99 ppm, based on tower volume.

On Aug. 11, 1986 three timed-release tablets containing a total of 300 g DBNPA were used to treat the tower. This is equivalent to a total dose of 53 ppm DBNPA. The tablets were placed in a shallow polyethylene tray which was submerged in the water directly below the fill. Slight water movement could be felt above the tray. Plate count data from samples taken before (pre-treatment data) and during (treatment data) treatment are given in Table 2. As these data show, the numbers of both fast and slow growing organisms were substantially lower during this phase of the experiment. This is true whether the comparison is made to the counts immediately prior to treatment (when no biocide was used) or to the counts obtained when treating the tower with daily slug doses of 3 ppm DBNPA.

During sampling on August 25th, it was noted that the fan was not operating and the entire volume of water in the system was hot. It was learned that the fan motor had malfunctioned sometime between August 23rd and 25th. As a result of the heating, the tablets melted and only a small residue remained (note that a visual examination of the tablets on August 22nd was made and an estimated half of the original tablet appeared to be intact). The residue was presumed due to the water-insoluble dicalcium phosphate dihydrate in the tablet. The tray and residue were removed from the tower on August 26th. Plate counts from samples taken August 25th and 26th indicated the tower to be essentially sterile (likely due to either the heat or the release of the remaining DBNPA).

Pre-treatment samples were taken again between August 27th and September 2nd and the tower was shown to be contaminated as would be expected with no biocide treatment. On September 2nd, three new tablets were placed in the tower in a manner similar to before. Subsequently, samples were taken five days per week and plate counts performed. The results of these pretreatment and treatment data are given in Table 3. At the conclusion of this study, the amount of DBNPA which remained was measured by HPLC and found to be approximately 4.5 grams, i.e. about 1.5 percent of the total original dose.

Based on the mean plate count data and the known or estimated total dose to the tower, the relative effectiveness of slug dosing vs. continuous dosing with timed-release tablets was calculated. The dose for the first tablet trial was estimated based on the fact that during the second trial similar tablets appeared to retain activity for approximately 21 days. Since accurate measurements could only be made during the first 11 days of the first tablet trial, the dose was estimated at 28 ppm DBNPA for the 11 day period, assuming that the overall release of DBNPA is linear.

The factors by which the planktonic plate counts were reduced, normalized for the difference in overall dose of DBNPA, were used to determine the relative biocidal activity. The relative effectiveness was shown to increase during use of the timed-release tablets by a factor of between 8 and 99 times. These data are summarized in Table 4. In general, it also appears that the increase in effectiveness is greater for faster growing organisms than for slower species. The data from 24 hour plate counts indicates that the potency increases by a factor of 33 to 99, whereas the same data for the slower growing population showed increased potency factor of 8 to 29.

These data do not take into account the ambient weather conditions in the calculation of effectiveness increase. Theoretically, a higher ambient temperature will cause an increased load on the tower and will result in a greater microbiological problem. If that is true, then the increase in effectiveness for timed-release tablets could be greater than these data indicate.

TABLE 1

Cooling Tower Treated with 3 ppm DBNPA/day, 7 Days per Week; Plate Count Summary

| Date | 24 hr Count | 48 hr Count | 72 hr Count |
| --- | --- | --- | --- |
| 04/29 | 780,000* | | 2,300,000 |
| 04/30 | 230,000 | | 830,000 |
| 05/01 | Pre-treatment data | | 1,900,000 |
| 05/02 | Treatment data | | 17,000 |
| 05/05 | 2,700 | 84,000 | 220,000 |
| 05/06 | 320,000 | 390,000 | 390,000 |
| 05/06 | 290,000 | | |
| 05/07 | 230,000 | 2,500,000 | 2,500,000 |
| 05/07 | 69,000 | 73,000 | 73,000 |
| 05/08 | 460,000 | 270,000 | |
| 05/08 | 29,000 | 120,000 | |
| 05/09 | 1,700,000 | 1,700,000 | 1,700,000 |
| 05/09 | 19,000 | 67,000 | 93,000 |
| 05/12 | 820,000 | 1,800,00 | 1,900,000 |
| 05/12 | 56,000 | 310,000 | 350,000 |
| 05/13 | 520,000 | 2,000,000 | 2,000,000 |
| 05/13 | 9,700 | 160,000 | 190,000 |
| 05/14 | 170,000 | 560,000 | 870,000 |
| 05/16 | 120,000 | 240,000 | 240,000 |
| 05/16 | 88,000 | 150,000 | 150,000 |
| 05/19 | 480,000 | 530,000 | 550,000 |
| 05/19 | 260,000 | 270,000 | 300,000 |
| 05/20 | 150,000 | 260,000 | 260,000 |
| 05/20 | 1,500 | 43,000 | 44,000 |
| 05/21 | 120,000 | 600,000 | 650,000 |
| 05/21 | 1,800 | 44,000 | 67,000 |
| 05/22 | 190,000 | 2,900,000 | 2,900,000 |

TABLE 1-continued

Cooling Tower Treated with 3 ppm DBNPA/day, 7 Days per Week; Plate Count Summary

| Date | 24 hr Count | 48 hr Count | 72 hr Count |
| --- | --- | --- | --- |
| 05/22 | 24,000 | 200,000 | 220,000 |
| 05/23 | 400,000 | 1,200,000 | 1,600,000 |
| 05/23 | 19,000 | 93,000 | 220,000 |
| 05/27 | 29,000 | 710,000 | 1,200,000 |
| 05/27 | 24,000 | 470,000 | 570,000 |
| 05/28 | 200,000 | 510,000 | 900,000 |
| 05/28 | 130,000 | 400,000 | 750,000 |
| 05/29 | 88,000 | 260,000 | 870,000 |
| 05/29 | 51,000 | 470,000 | 660,000 |
| 05/30 | 41,000 | 340,000 | 1,400,000 |
| 05/30 | 30,000 | 310,000 | 1,100,000 |
| 06/02 | 20,000 | 110,000 | 850,000 |
| 06/02 | 9,600 | 170,000 | 270,000 |
| 06/03 | 340,000 | 720,000 | 930,000 |
| 06/03 | 79,000 | 600,000 | 680,000 |
| Mean | 199,771 | 596,865 | 679,000 |

(Treatment Data)

*Numbers refer to colony forming units

TABLE 2

Cooling Tower Treated with 3 Timed-Released DBNPA Tablets Plate Count Summary (Total Dose Equals 53 ppm)

| Date | 24 hr Count | 48 hr Count | 72 hr Count |
| --- | --- | --- | --- |
| 08/05 | 29,000* | 1,100,000 | 1,200,000 |
| 08/05 | 38,000 | 1,100,000 | 1,400,000 |
| 08/06 | 36,000 | 980,000 | 1,000,000 |
| 08/06 | 35,000 | 1,000,000 | 1,000,000 |
| 08/07 | 12,000 | | |
| 08/07 | 17,000 | | |
| 08/11 | 19,000 | 110,000 | 140,000 |
| Pre-treatment data | | | |
| Treatment data | | | |
| 08/12 | 11,000 | 120,000 | 200,000 |
| 08/13 | 6,000 | 140,000 | 170,000 |
| 08/14 | 4,300 | 32,000 | 60,000 |
| 08/14 | 4,300 | 55,000 | 100,000 |
| 08/15 | 4,000 | 48,000 | 52,000 |
| 08/15 | 3,700 | 33,000 | 42,000 |
| 08/18 | 15,000 | 93,000 | 100,000 |
| 08/19 | 7,800 | 53,000 | 58,000 |
| 08/20 | 4,800 | 63,000 | 98,000 |
| 08/21 | 8,700 | 97,000 | 130,000 |
| 08/22 | 8,700 | 72,000 | 100,000 |

Fan stopped on weekend of 8/23–8/24. Water got hot. Tablets melted. Plate counts after cessation of treatment showed tower became heavily contaminated.

| Mean | 7,118 | 73,273 | 100,909 |

(Treatment Data)

*Numbers refer to colony forming units.

TABLE 3

Cooling Tower Treated with 3 Timed-Released DBNPA Tablets Plate Count Summary (Total Dose Equals 53 ppm)

| Date | 24 hr Count | 48 hr Count | 72 hr Count |
| --- | --- | --- | --- |
| 08/27 | 98,000* | 700,000 | |
| 08/28 | 720,000 | 1,000,000 | |
| 08/29 | 52,000 | 60,000 | |
| 09/02 | 48,000 | 330,000 | 600,000 |
| Pre-treatment data | | | |
| Treatment data | | | |
| 09/03 | 10,000 | 75,000 | 250,000 |
| 09/04 | 17,000 | 110,000 | 380,000 |
| 09/05 | 5,700 | 11,000 | 87,000 |
| 09/08 | 11,000 | 68,000 | 75,000 |
| 09/09 | 5,000 | 55,000 | 770,000 |
| 09/10 | 9,700 | 72,000 | 280,000 |
| 09/11 | 22,000 | 55,000 | 180,000 |
| 09/12 | 13,000 | 50,000 | 83,000 |
| 09/15 | 15,000 | 35,000 | |
| 09/16 | <50** | <50** | 1,200** |
| 09/18 | 14,300 | 45,000 | 100,000 |

TABLE 3-continued

Cooling Tower Treated with 3 Timed-Released DBNPA Tablets Plate Count Summary (Total Dose Equals 53 ppm)

| Date | 24 hr Count | 48 hr Count | 72 hr Count |
| --- | --- | --- | --- |
| 09/19 | 4,500 | 52,000 | 130,000 |
| 09/22 | 7,500 | 18,000 | 22,000 |
| 09/23 | 25,000 | 88,000 | 170,000 |
| 09/24 | 80,000 | 200,000 | 350,000 |
| 09/25 | 95,000 | 420,000 |  |
| 09/26 | 130,000 | 140,000 |  |
| 09/29 | 13,000 |  |  |
| Mean | 11,411 | 53,733 | 183,086 |

(Treatment Data)

*Numbers refer to colony forming units
**Due to weather conditions, flow over tower was discontinued and sample for this count was taken from the basin.

TABLE 4

Comparison of plate counts taken during intermittent dosing and dosing with DBNPA containing tablets.

| | |
| --- | --- |
| Note: | Total dose during intermittent dosing was 3 ppm/day × 33 days = 99 ppm DBNPA. Total estimated dose from first tablet trial = 28 ppm DBNPA, based on the fact that 11 days elapsed and that the 53 ppm tablet has been observed to remain effective for 21 days. Total dose from the second tablet trial = 53 ppm. |
| 24 Hour Data: | Mean for intermittent dosing = 199,771 CFU/ml<br>Mean for first tablet trial = 7,118 CFU/ml<br>Effectiveness increased by 99 times.*<br>Mean for second tablet trial = 11,411 CFU/ml<br>Effectiveness increased by 33 times.* |
| 48 Hour Data: | Mean for intermittent dosing = 596,865 CFU/ml<br>Mean for first tablet trial = 73,273 CFU/ml<br>Effectiveness increased by 29 times.*<br>Mean for second tablet trial = 53,773 CFU/ml<br>Effectiveness increased by 21 times.* |
| 72 Hour Data: | Mean for intermittent dosing = 769,000 CFU/ml<br>Mean for first tablet trial = 100,9009 CFU/ml<br>Effectiveness increased by 27 times.*<br>Mean for second tablet trial = 183,086 CFU/ml<br>Effectiveness increased by 8 times.* |

*The increase in effectiveness was calculated based on the difference in mean plate counts and difference in total dose, as follows:

$$\frac{PC\ (tablets)}{PC\ (slug)} \times \frac{Total\ dose\ (slug)}{Total\ dose\ (tablet)} = Increase\ Factor,$$

where PC = mean plate count, i.e., mean number of organisms based on the number of colony forming units

What is claimed is:

1. A solid antimicrobial composition consisting essentially of:
   (a) about 1 to about 90 percent by weight of a halogenated amide antimicrobial compound of the formula

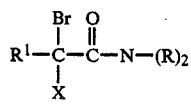

wherein
X is hydrogen, halogen of a cyano radical;
each R group is independently hydrogen, a monovalent saturated hydrocarbon radical or an inertly substituted monovalent saturated hydrocarbon radical or the two R groups are, jointly, a divalent saturated hydrocarbon radical, or an inertly substituted divalent saturated hydrocarbon radical, which, taken with the adjacent nitrogen atom, forms a heterocyclic ring having from 4 to about 10 ring members; and $R^1$ is a cyano radical or an amido radical having the formula:

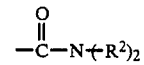

wherein $R^2$ has the same meaning as R;
   (b) about 10 to about 80 percent by weight of a suitable hydrophilic polymer selected from the group consisting of a natural water soluble cellulosic polymer, a synthetic water soluble cellulosic polymer, gelatin, maltodextrin, xanthan gum, carrageenan, carboxymethyl guar, hydroxypropyl guar and carboxymethyl galactomannose;
   (c) about 0 to about 80 percent by weight of a compression agent; and
   (d) about 0 to about 10 percent by weight of a mold release agent.

2. The antimicrobial composition of claim 1 wherein the suitable hydrophilic polymer is methyl cellulose or hydroxypropyl methyl cellulose.

3. The composition of claim 1 wherein X is hydrogen, chlorine or bromine, $R^1$ is cyano, and each R is independently hydrogen, lower alkyl or phenyl.

4. The composition of claim 1 wherein X is hydrogen or bromine, $R^1$ is cyano, and each R is independently hydrogen or methyl.

5. The composition of claim 1 wherein said halogenated amide antimicrobial compound is selected from the group consisting of 2-bromo-3-nitrilopropionamide, 2-bromo-2,3-dinitrilopropionamide, 2,2-dibromo-3-nitrilopropionamide, N-(n-butyl)-2-bromo-3-nitrilopropionamide; N,N-dimethyl-2,2-dibromo-3-nitrilopropionamide, 2-chloro-2-bromo-3-nitrilopropionamide, N-(n-propyl)-2-iodo-2-bromo-3-nitrilopropionamide, N-methyl-N-ethyl-2-fluoro-2-bromo-3-nitrilopropionamide, N-phenyl-2-cyano-2-bromo-3-nitrilopropionamide, N-cyclohexyl-2,2-dibromo-3-nitrilopropionamide, N-benzyl-2-bromo-3-nitrilopropionamide, N-(2,2-dibromo-3-nitrolopropionoyl)-piperidine, 2-bromomalonic diamide, 2-2-dibromomalonic diamide, N-methyl-N'-ethyl-2-chloro-2-bromomalonic diamide, N-phenyl-2-iodo-2-bromomalonic diamide, N-methyl-2-bromo-3-nitrilopropionamide, N-phenyl-2-bromo-2-chloro-3-nitrilopropionamide, N-methyl-2,2-dibromo-3-nitrilopropionamide, N,N-dimethyl-2-bromo-3-nitrilopropionamide, N,N-diethyl-2,2-dibromo-3-nitrilopropionamide, N-(n-butyl-2,2-dibromo-3-nitrilopropionamide, and N-phenyl-N-methyl-2,2-dibromo-3-nitrilopropionamide.

6. The composition of claim 1 wherein said halogenated amide antimicrobial compound is 2,2-dibromo-3-nitrilopropionamide.

7. The composition of claim 1 wherein the hydrophilic polymer is hydroxypropyl methyl cellulose.

8. The composition of claim 7 wherein the hydrophilic polymer is hydroxypropyl methyl cellulose.

9. The composition of claim 1 wherein the compression agent is lactose and the mold release agent is stearic acid.

10. The composition of claim 8 wherein the compression agent is lactose and the mold release agent is stearic acid.

11. The composition of claim 1 comprising
   (a) about 10 to about 50 percent by weight of a halogenated amide antimicrobial compound, (b) about 20 to about 50 percent by weight of the hydrophilic polymer,
(c) about 5 to about 80 percent by weight of a compression agent, and
(d) about 0 to about 5 percent by weight of a mold release agent.

12. The composition of claim 1 comprising
(a) about 30 to about 50 percent by weight of a halogenated amide antimicrobial compound,
(b) about 20 to about 40 percent by weight of the hydrophilic polymer,
(c) about 20 to about 40 percent by weight of a compression agent, and
(d) about 0 to about 4 percent by weight of a mold release agent.

13. The composition of claim 12 wherein the halogenated amide antimicrobial compound is 2,2-dibromo-3-nitrilopropionamide, the suitable hydrophilic polymer is hydroxypropylmethyl cellulose, the compression agent is lactose, and the mold release agent is stearic acid.

14. The composition of claim 1 that is in tablet form.

15. A method for biological control in an aqueous industrial system in need of such control comprising contacting said system with an antimicrobially effective amount of the solid antimicrobial composition as defined in claim 1.

16. A method for biological control in an aqueous industrial system in need of such control comprising contacting said system with an antimicrobially effective amount of the solid antimicrobial composition as defined in claim 2.

17. A method for biological control in an aqueous industrial system in need of such control comprising contacting said system with an antimicrobially effective amount of the solid antimicrobial composition as defined in claim 3.

18. A method for biological control in an aqueous industrial system in need of such control comprising contacting said system with an antimicrobially effective amount of the solid antimicrobial composition as defined in claim 4.

19. A method for biological control in an aqueous industrial system in need of such control comprising contacting said system with an antimicrobially effective amount of the solid antimicrobial composition as defined in claim 5.

20. A method for biological control in an aqueous industrial system in need of such control comprising contacting said system with an antimicrobially effective amount of the solid antimicrobial composition as defined in claim 6.

21. A method for biological control in an aqueous industrial system in need of such control comprising contacting said system with an antimicrobially effective amount of the solid antimicrobial composition as defined in claim 7.

22. A method for biological control in an aqueous industrial system in need of such control comprising contacting said system with an antimicrobially effective amount of the solid antimicrobial composition as defined in claim 8.

23. A method for biological control in an aqueous industrial system in need of such control comprising contacting said system with an antimicrobially effective amount of the solid antimicrobial composition as defined in claim 9.

24. A method for biological control in an aqueous industrial system in need of such control comprising contacting said system with an antimicrobially effective amount of the solid antimicrobial composition as defined in claim 10.

25. A method for biological control in an aqueous industrial system in need of such control comprising contacting said system with an antimicrobially effective amount of the solid antimicrobial composition as defined in claim 11.

26. A method for biological control in an aqueous industrial system in need of such control comprising contacting said system with an antimicrobially effective amount of the solid antimicrobial composition as defined in claim 12.

27. A method for biological control in an aqueous industrial system in need of such control comprising contacting said system with an antimicrobially effective amount of the solid antimicrobial composition as defined in claim 13.

28. The method of claim 15 wherein the aqueous industrial system is a cooling tower, metalworking fluid, pulp and paper system, or air washer.

* * * * *